(12) United States Patent
Fan

(10) Patent No.: US 9,731,130 B2
(45) Date of Patent: Aug. 15, 2017

(54) FLEXIBLE ARTIFICIAL RETINA DEVICE

(71) Applicant: Long-Sheng Fan, Hsinchu (TW)

(72) Inventor: Long-Sheng Fan, Hsinchu (TW)

(73) Assignee: IRIDIUM MEDICAL TECHNOLOGY CO, LTD., Hsinchu (TW)

( * ) Notice: Subject to any disclaimer, the term of this patent is extended or adjusted under 35 U.S.C. 154(b) by 0 days.

(21) Appl. No.: 14/948,235

(22) Filed: Nov. 20, 2015

(65) Prior Publication Data

US 2016/0074659 A1 Mar. 17, 2016

Related U.S. Application Data

(60) Continuation of application No. 14/084,482, filed on Nov. 19, 2013, now Pat. No. 9,224,716, which is a
(Continued)

(51) Int. Cl.
*A61N 1/36* (2006.01)
*H01L 27/146* (2006.01)
(Continued)

(52) U.S. Cl.
CPC ............ *A61N 1/36046* (2013.01); *A61F 2/14* (2013.01); *H01L 24/75* (2013.01); *H01L 24/83* (2013.01);
(Continued)

(58) Field of Classification Search
None
See application file for complete search history.

(56) References Cited

U.S. PATENT DOCUMENTS 5,476,494 A 12/1995 Edell et al.
5,650,363 A 7/1997 Endroes et al.
(Continued)

FOREIGN PATENT DOCUMENTS

JP 07283365 A 10/1995
JP 318218 A 11/2003
JP 2006-051164 2/2006

OTHER PUBLICATIONS

Fan, L.-S. et al., "Monolithically Integrated Flexible Artificial Retina Microsystems Technology and in vitro Characterization," Association for Research in Vision and Ophthalmology, ARVO 2010, May 2-6, 2010, Ft. Lauderdale, Florida, USA, abstract.
(Continued)

*Primary Examiner* — Brian T Gedeon
(74) *Attorney, Agent, or Firm* — Blakely, Sokoloff, Taylor & Zafman LLP

(57) ABSTRACT

An implant apparatus comprising a plurality of photo sensors, a plurality of micro electrodes, a plurality of guard rings surrounding the micro electrodes and circuitry coupled to the photo sensors and the micro electrodes are described. The photo sensors may receive incoming light. The circuit may drive the micro electrodes to stimulate neuron cells for enabling perception of a vision of the light captured by the photo sensors. The guard rings may confine electric flows from the micro electrodes to the targeted neuron cells. The apparatus may be implemented in a flexible material to conform to a shape of a human eyeball to allow the micro electrodes aligned with the neuron cells for the stimulation.

23 Claims, 12 Drawing Sheets

Related U.S. Application Data division of application No. 13/300,547, filed on Nov. 18, 2011, now Pat. No. 8,613,135, and a continuation-in-part of application No. 13/282,422, filed on Oct. 26, 2011, now Pat. No. 8,530,265, which is a continuation-in-part of application No. 13/102,596, filed on May 6, 2011, now abandoned.

(60) Provisional application No. 61/553,919, filed on Oct. 31, 2011.

(51) Int. Cl.
*H01L 23/00* (2006.01)
*A61F 2/14* (2006.01)
*A61N 1/05* (2006.01)

(52) U.S. Cl.
CPC ...... *H01L 27/14618* (2013.01); *A61N 1/0543* (2013.01); *H01L 2924/13091* (2013.01); *Y10T 29/4913* (2015.01); *Y10T 29/49117* (2015.01); *Y10T 29/49126* (2015.01); *Y10T 29/49144* (2015.01); *Y10T 29/49155* (2015.01)

(56) References Cited

U.S. PATENT DOCUMENTS

| | | | |
|---|---|---|---|
| 5,840,199 | A | 11/1998 | Warren |
| 6,068,632 | A | 5/2000 | Carchidi |
| 6,294,831 | B1 | 9/2001 | Shishido et al. |
| 6,324,429 | B1 | 11/2001 | Shire et al. |
| 6,392,143 | B1 | 5/2002 | Koshio |
| 7,035,692 | B1 | 4/2006 | Maghribi et al. |
| 7,079,900 | B2 | 7/2006 | Greenburg et al. |
| 7,091,619 | B2 | 8/2006 | Aoyagi |
| 7,113,661 | B2 | 9/2006 | Arai et al. |
| 7,127,301 | B1 | 10/2006 | Okandan et al. |
| 7,130,693 | B1 | 10/2006 | Montalbo |
| 7,158,836 | B2 | 1/2007 | Suzuki |
| 7,840,274 | B2 | 11/2010 | Greenberg et al. |
| 7,914,842 | B1 | 3/2011 | Greenberg et al. |
| 8,142,190 | B2 | 3/2012 | Anitua Aldecoa |
| 8,150,526 | B2 | 4/2012 | Gross et al. |
| 8,209,023 | B2 | 6/2012 | Zhou et al. |
| 8,322,027 | B1 | 12/2012 | Greenberg et al. |
| 2002/0091422 | A1 | 7/2002 | Greenberg et al. |
| 2002/0094508 | A1 | 7/2002 | Lorenzi |
| 2002/0099420 | A1 | 7/2002 | Chow et al. |
| 2002/0111655 | A1 | 8/2002 | Scribner |
| 2003/0114904 | A1 | 6/2003 | Ovadia et al. |
| 2003/0160303 | A1 | 8/2003 | Hirokawa et al. |
| 2003/0209792 | A1 | 11/2003 | Takaishi |
| 2005/0082684 | A1 | 4/2005 | Aiba et al. |
| 2005/0161818 | A1 | 7/2005 | Basceri |
| 2006/0184245 | A1 | 8/2006 | Graf et al. |
| 2006/0241753 | A1 | 10/2006 | Suaning et al. |
| 2006/0273304 | A1 | 12/2006 | Cok |
| 2007/0142877 | A1 | 6/2007 | McLean |
| 2007/0257373 | A1 | 11/2007 | Akram et al. |
| 2008/0058897 | A1 | 3/2008 | McMahon et al. |
| 2008/0065208 | A1 | 3/2008 | Greenberg et al. |
| 2008/0086206 | A1 | 4/2008 | Nasiatka et al. |
| 2008/0288067 | A1 | 11/2008 | Flood |
| 2008/0294224 | A1 | 11/2008 | Greenberg et al. |
| 2009/0264972 | A1 | 10/2009 | Zhou et al. |
| 2009/0326594 | A1 | 12/2009 | North et al. |
| 2010/0184285 | A1 | 7/2010 | Hua et al. |
| 2010/0204754 | A1 | 8/2010 | Gross et al. |
| 2010/0298895 | A1 | 11/2010 | Ghaffari et al. |
| 2011/0108180 | A1 | 5/2011 | Fendler et al. |
| 2011/0172736 | A1 | 7/2011 | Gefen et al. |
| 2011/0307042 | A1 | 12/2011 | DeCarmine |

OTHER PUBLICATIONS

Fan, Long-Sheng et al., "A Flexible & Translucent CMOS Retinal Prosthesis and in vitro Characterization," Association for Research in Vision and Ophthalmology, ARVO 2011, May 1-5, 2011, Ft. Lauderdale, Florida, USA, abstract.

Fan, L.-S. et al., "A Flexible Sensing CMOS Technology for Sensor-Integrated, Intelligent Retinal Prosthesis," Asia-Pacific Conference on Vision, APCV 2010, Jul. 23-26, 2010, Taipei, Taiwan, abstract.

Zrenner, Eberhart et al., "Subretinal electronic chips allow blind patients to read letters and combine them to words," Proceedings of the Royal Society B, 2011, 278, 1489-1497, downloaded from http://rspb.royalsocietypublishing.org/, Jul. 18, 2011.

Shire, Douglas B. et al., "Development and Implantation of a Minimally Invasive Wireless Subretinal Neurostimulator," IEEE Transactions on Biomedical Engineering, vol. 56, No. 10, Oct. 2009.

Ahuja, A. K., et al., "Blind subjects implanted with the Argus II retinal prosthesis are able to improve performance in a spatial-motor task," British Journal of Ophthalmology, 95:539-543, Sep. 29, 2010, downloaded from http://bjo.bmj.com/, Jul. 28, 2011.

Ng, David C. et al., "Implantable Microimagers," Sensors 2008, 8(5), 3183-3204, May 15, 2008.

Tokuda, Takashi et al., "Flexible and extendible neural interface device based on cooperative multi-chip CMOS LSI architecture," Sensors and Actuators A 122 (2005), 88-98, May 25, 2005.

International Search Report and Written Opinion mailed Jul. 6, 2012, for International Patent Application No. PCT/US2011/064014, 18 pages.

"PCT Notification of Transmittal of the International Search Report and the Written Opinion of the International Searching Authority for PCT Application No. PCT/US2011/058159", (Apr. 25, 2012), 19 pages.

Late Breaking Abstracts. For Sight: The Future of Eye and Vision Research, The Association for Research in Vision and Opthalmology (ARVO), Session #570-#6414-6457 (D1032-D1075), (May 2-6, 2010), 8 pages.

Chichilnisky, et al., "Functional Asymmetries in ON and OFF Ganglion Cells of Primate Retina", The Journal of Neuroscience, 22(7), (Apr. 1, 2002), pp. 2737-2747.

Graf, Heinz-Gerd, "Bendable Electronics for Retinal Implants", Ultra-thin Chip Technology and Applications, Chapter 28, Springer New York, (Nov. 12, 2010), pp. 363-375.

200A

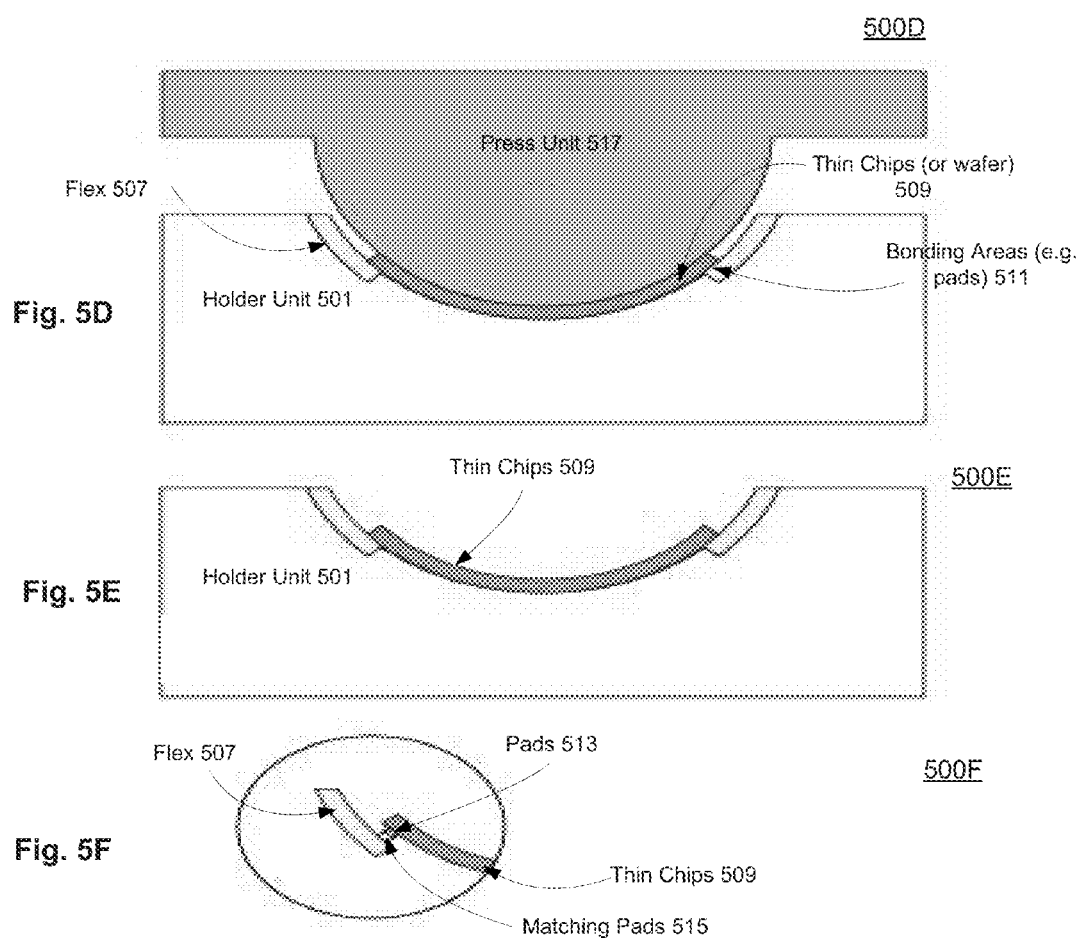

FLEXIBLE ARTIFICIAL RETINA DEVICE

RELATED APPLICATIONS

This application is a continuation application of a co-pending U.S. patent application Ser. No. 14/084,482, filed Nov. 19, 2013, which is a divisional application of U.S. patent application Ser. No. 13/300,547, filed Nov. 18, 2011, now U.S. Pat. No. 8,613,135, which claims the benefit of Provisional Patent Application No. 61/553,919, filed on Oct. 31, 2011 and is a continuation in part (CIP) application of U.S. patent application Ser. No. 13/282,422 filed on Oct. 26, 2011, now U.S. Pat. No. 8,530,265, which is a CIP application of U.S. patent application Ser. No. 13/102,596 filed on May 6, 2011. The disclosure of the above applications is incorporated by reference herein in their entirety.

FIELD OF INVENTION

The present invention relates generally to assembly process of micro devices, and more particularly to assembly of three-dimensional curved flexible device chips.

BACKGROUND

Integrated electronic circuit (IC) industry relies on "planar" technology to reduce the limit of feature size of photolithography and to progress according to Moore's law, since the depth of focus is reduced when the numerical aperture is increased to define finer features in photolithography. However, planar surfaces of devices based on such planar technologies may limit geometry of interactions and/or interconnections among these devices or with an external system or external systems.

Thus, traditional planar technologies may not be capable of providing devices with non-planar geometries to minimize complexity of interactions among the devices or with external systems.

SUMMARY OF THE DESCRIPTION

In one embodiment, an assembly method for non-planar (e.g. quasi-spherical) structures, such as non-planar surface patch of a semiconductor chip (or chip stack) may comprise depositing stressed films on either side (or both sides) of a thin semiconductor substrate of a thin chip for small deformations of the chip. Stressed films may be deposited with patterning of the stressed films (for example, by using photolithography and etching or lift-off process) for small deformations with controlled shapes. Alternatively, slots may be created on thin chips and stressed films may be deposited to allow large deformation of the chip.

In another embodiment, "slots" may be created on thin chips and the chips may be bonded to a separate piece of a constraining element (for example, a ring-shaped patch or another chip) to allow larger deformation of the chips. The "slot" can be formed by continuous opening with varying width extended from a location within the chip to a chip edge that creates new straight or curved edges and sidewalls for the local structure and allows certain lateral displacements when the local structure is under bending or deforming stresses. The bonding may be mechanically constraining and optionally providing electrical connections between bonded pieces of elements across slots (including the chips). A combination of slots with stressed films and constraining elements can form a curved surface for the chips. Two or more slotted pieces of the chips may be bonded to have mutual or multiple constraints to hold curved pieces in place. In some embodiments, curved structures thus formed may be suitable for brain-machine interfaces (such as retinal prosthesis), or new architectures of 3D (three dimensional) interconnections of signal processing units.

An embodiment of the present invention includes methods and apparatuses for assembly of a non-planar device based on curved chips. Slots may be created as longitudinal openings in the chips to reduce bending stresses to increase allowable degrees of deformation of the chips. The chips may be deformed to a desired deformation within the allowable degrees of deformation via the slots. Holding constraints may be provided on at least a portion of the chips to allow the chips to remain curved according the desired deformation.

In another embodiment, curved chips can include multiple chips. One chip (e.g. a first one of the chips) may be curved to a desired deformation. Another chip (e.g. a second one of the chips) may be deformed to conform to the desired deformation of the first chip. The deformed chips may be bonded with each other with a continuous piece of one chip across the slot of another chip to provide holding constraints between these chips to allow these chips to remain curved in the desired deformation.

In yet another embodiment, an assembly apparatus for non-planar curved chips may comprise a set of pressure units, a holder unit and a control unit. The pressure units may have a first surface curved according to a desired curvature. The holder unit may have a second surface curved conforming to the desired curvature. The control unit may control movement of the pressure unit and the holder unit. The pressure unit may be configured to deform the chips to the desired curvature over the first surface. The holder unit may be configured to deform fixture structures according to the desired curvature over the second surface. The control unit may be configured to cause the pressure unit and the holder unit to bond the chips with the fixture structures between the first surface and the second surface via the movement of the pressure unit. The bonding may provide holding constraints for the chips and the fixture structures to remain curved.

Other features of the present invention will be apparent from the accompanying drawings and from the detailed description that follows.

BRIEF DESCRIPTION OF THE DRAWINGS

The present invention is illustrated by way of example and not limitation in the figures of the accompanying drawings, in which like references indicate similar elements and in which:

FIGS. 5A-5F are block diagrams illustrating an exemplary sequence of assembly process for a non-planar flexible device;

DETAILED DESCRIPTION

Figure 1A:
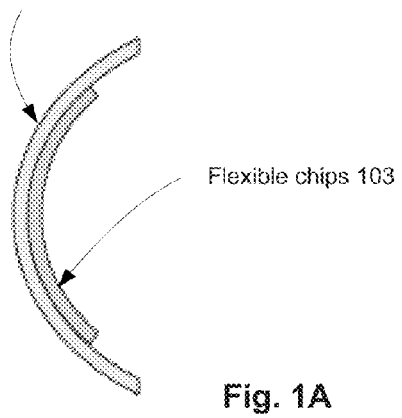
FIGS. 1A-1D are schematic diagrams illustrating exemplary embodiments of non-planar assembly for flexible chips.

Retina chip assembly processes or non-planar (such as quasi-spherical) surface patches of (integrated) semiconductor chips and methods are described herein. In the following description, numerous specific details are set forth to provide thorough explanation of embodiments of the present invention. It will be apparent, however, to one skilled in the art, that embodiments of the present invention may be practiced without these specific details. In other instances, well-known components, structures, and techniques have not been shown in detail in order not to obscure the understanding of this description.

Reference in the specification to "one embodiment" or "an embodiment" means that a particular feature, structure, or characteristic described in connection with the embodiment can be included in at least one embodiment of the invention. The appearances of the phrase "in one embodiment" in various places in the specification do not necessarily all refer to the same embodiment.

In one embodiment, it is advantageous to have non-planar surfaces of integrated active devices, transistor circuits, transducers or micro systems, to change the geometry of interactions, interconnections among these devices, subsystems, or interactions, interconnections with an external system, or external systems. Integrated devices with non-planar shapes or geometries may enable new computational architectures (such as a ball-shaped geometry is a "round-table forum" in 3D optimizing the interactions, communications, and interconnections between computational elements on the surfaces, and communication/interaction link inside the sphere). It enables new ways of interfacing electronics or photonics to biological neural systems in general (such as in the brain-machine interface (BMI), quasi-spherical surfaces are frequently encountered).

For example, in the case of an artificial retina, the interface between the prosthesis device and the retina at the back of a human eyeball is a quasi-spherical surface with a radius of curvature of ~12.5 mm. To minimize the complexity of interconnections through eyeballs, it is desirable to collocate the interfacing micro electrodes and electronic circuitry, and together in close proximity to the surface of retina neurons. This disclosure teaches the method to form the typically rigid semiconductor electronics into the non-planar (here, quasi-spherical) shape.

FIGS. 1A-1D are schematic diagrams illustrating exemplary embodiments of non-planar assembly for flexible chips. Assembly 100A of FIG. 1A may illustrate an artificial retinal prosthesis device in a quasi-spherical shape conforming to the shape of the retina in an eyeball to allow the device positioned in close proximity to the surface of retina neurons. The conformity of the shape thus may reduce the required electrical excitation thresholds of neurons and increases the granularity of the interface between the device (e.g. via electrodes) and the retina neurons.

In one embodiment, assembly 100A may comprise flexible chips 103 with light sensors, electrodes, driving circuits, etc. Flexible chips 103 may be mechanically constrained to be curved in a desired shape or deformation via fixture structure 101. For example, fixture structure 101 may comprise a flexible polymer material shaped or deformed with a desired curvature. Flexible chips 103 may be bonded or fixed to fixture structure 101 to remain curved in the desired shape.

Figure 1B:
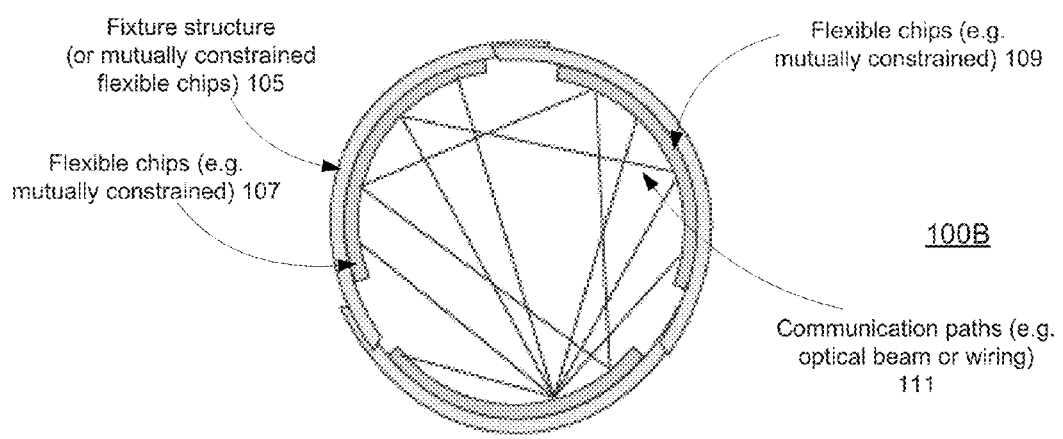

Turning now to FIG. 1B, assembly 100B may be a relatively spherical-shaped assembly comprising multi-layers of flexible chips. For example, flexible chips 107, 109 may be deformed to facilitate communications among surface elements of the chips 107, 109. Chips 107, 109 may be positioned or configured to face each other to establish communication paths, such as communication path 111, using either optical beams, wirings or other applicable connections. In some embodiments, a communication path between different curved chips facing in the same direction (such as ships 105, 107) may be based on through-silicon via. The through silicon via may bring some pads of a thin IC chip through its thin silicon substrate to the backside (e.g. from front side) of the thin IC chip so multiple chips can be stacked and bonded together. Multiple chips, such as fixture structure 105, flexible chips 107, may remain curved in assembly 100B based on mutual constraints between these chips.

The non-planar geometry of assembly 100B may enable computational architectures based on connections or other applicable non-planner shaped features. For example, a ball-shaped geometry in a sphere assembly may be a "round-table forum" in 3D (three dimensional) geometry for optimizing the interactions, communications, and interconnections between computational elements (or circuitry of flexible chips) on the surfaces of the sphere assembly, and communication/interaction links for elements located inside the sphere assembly.

Figure 1C:
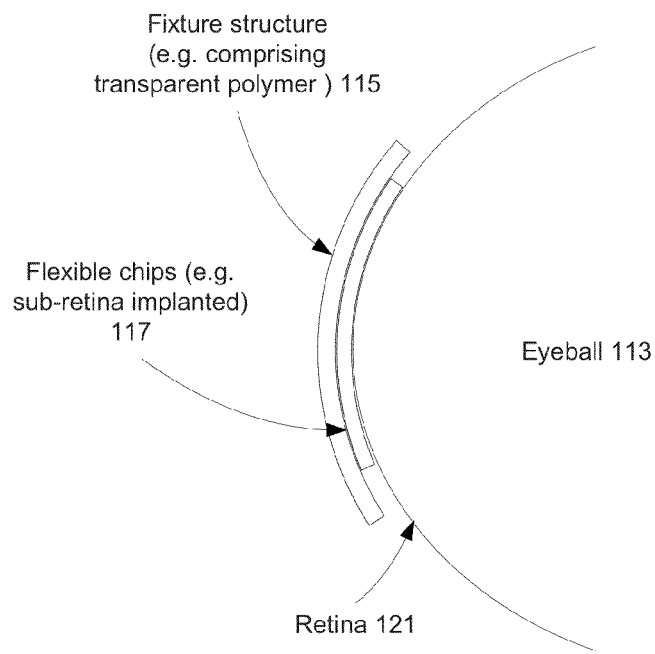

Turning now to FIG. 1C, a non-planar artificial retina assembly may be implanted for eyeball 113 in a sub-retina manner. The artificial retina may include flexible chips 117 in close contact with retina 121 of eyeball 113. Flexible chips 117 may be bonded with fixture structure 115 to remain curved to conform to the shape of eyeball 113. In one embodiment, both fixture structure 115 and flexible chips 117 may comprise transparent material to allow light to pass through.

Figure 1D:
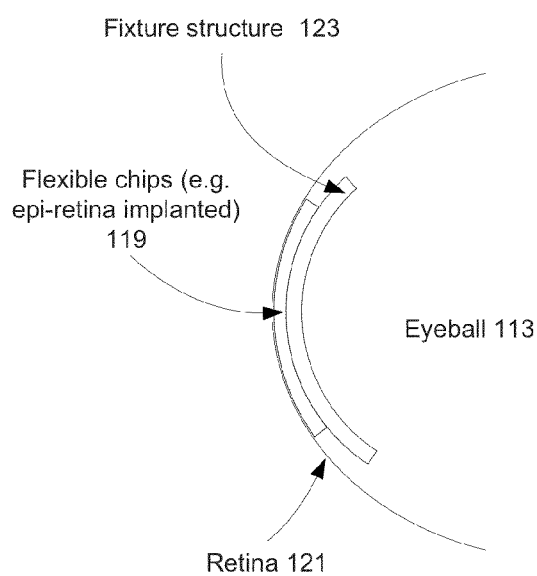

Alternatively, in FIG. 1D, a non-planar artificial retina assembly may be implanted for eyeball 113 in an epi-retina manner. The artificial retina may include flexible chips 119 in close contact with retina 121 from inside of eyeball 113. In addition, the artificial retina may include fixture structure 123 to provide mechanical constraints to allow flexible chips 119 to remain curved conforming to the shape of eyeball 113. The non-planar artificial retina assembly may be flexible so as to be deformed according to various configurations or shapes desired.

Figure 2A:
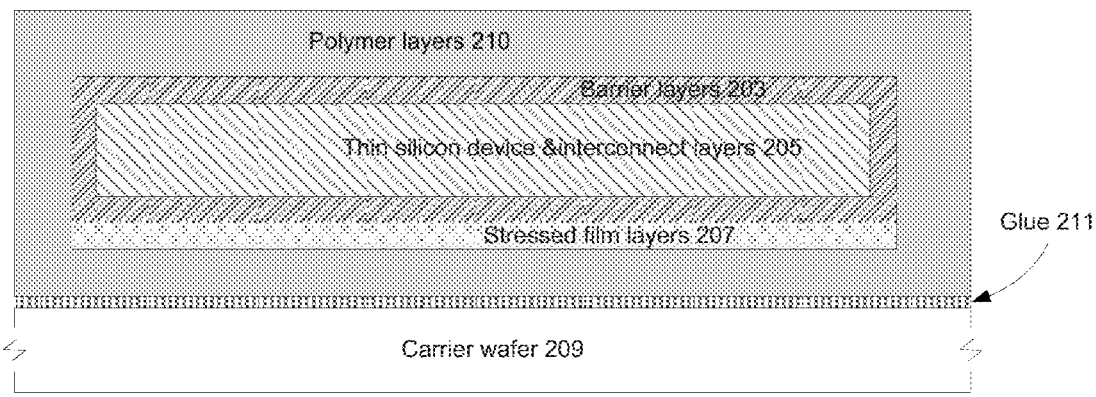
FIG. 2A is a block diagram illustrating cross sectional views of a flexible structure deposited with a stressed thin film according to embodiments described herein.

FIG. 2A is a block diagram illustrating cross sectional views of a flexible structure (or device) deposited with a stressed thin film. In one embodiment, structure 200 may include thin device layers 205 sandwiched between barrier layers 203 and polymers 210. Device layers 205 may be based on a thin MOS (Metal Oxide Semiconductor) die intended for medical implant wrapped by barrier layers 203 and biocompatible polymer layers 210 to protect against device corrosion and/or poisoning living tissues. Structure 200A may be thin enough to curl (or bend, deform) according to stress or stretching force from stressed film layers 207.

In some embodiments, stressed thin films, such as stressed film layers 207, may be deposited in either side or both sides of a thin structure or chip to achieve desired deformation (e.g. with a certain degrees bending) for the chip. For example, stressed thin films may be pre-compressed or pre-stretched to apply bending force in different directions. Optionally, stressed thin films can be patterned (for example, in annular shapes or long stripes by photolithography and etching processes) during the fabrication process to create various curved shapes (e.g. in a wavy manner or other applicable forms) for the thin structure. Structure 200 may curl when released from thick carrier wafer (or handle wafer) 209 attached via glue 211.

Figure 2B:
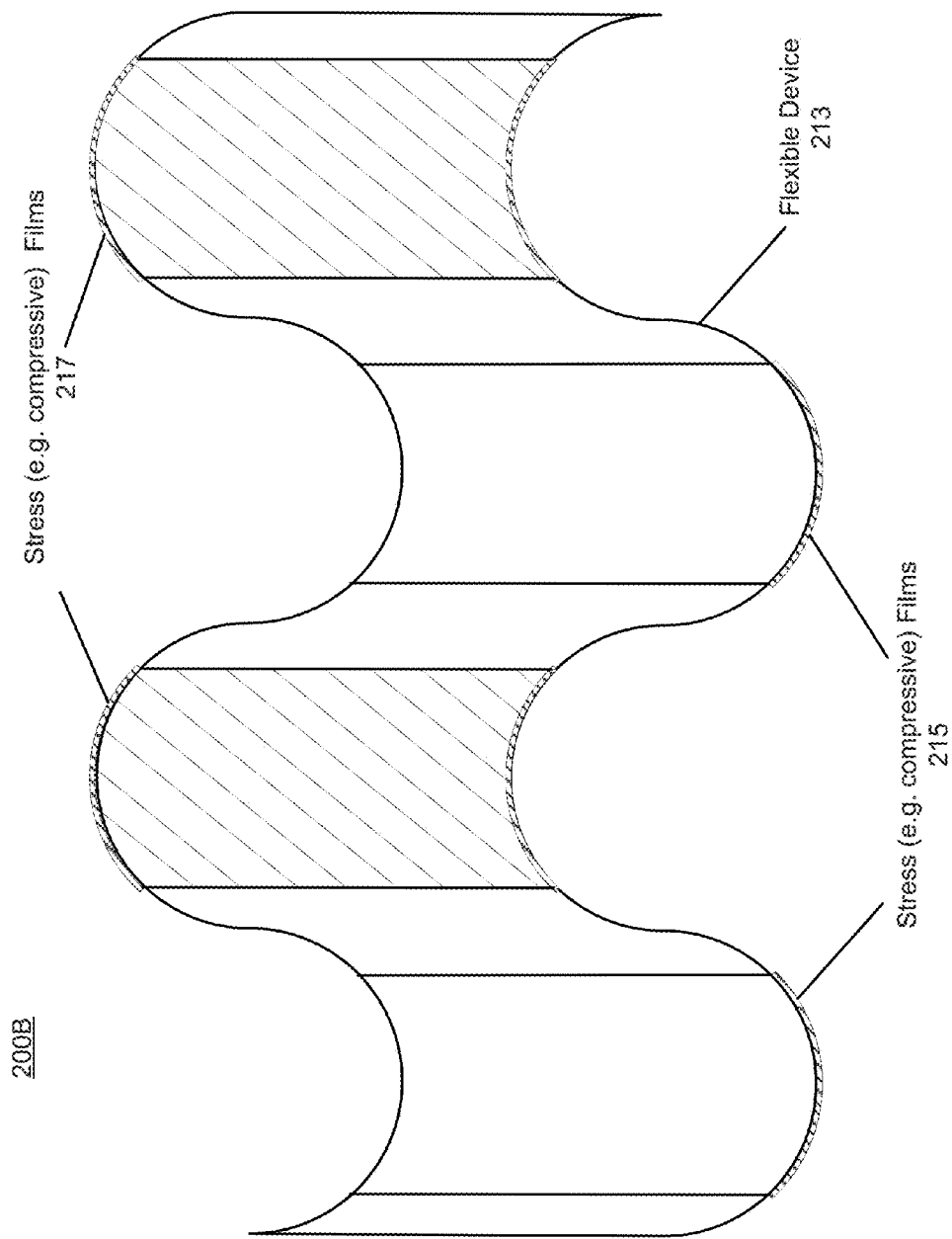
FIG. 2B is a schematic diagram illustrating a non-planar device deformed in a wavy manner according to embodiments described herein.

FIG. 2B is a schematic diagram illustrating a non-planar device deformed in a wavy manner according to embodiments described herein. For example, non-planner integrated circuit device 200B may include a flexible thin structure 213 curved in a wavy manner. Stressed films 215, 217 may be formed (e.g. via pattern masks) on both sides of structure 213 to form a specific (or pre-designated) pattern (e.g. stripes, zigzag, or other applicable patterns etc.) to curve structure 213 in a desired deformation, such as a wavy manner. In one embodiment, stress film 215 may be pre-compressed or compressive. Alternatively, stress films may be pre-stretched. Stress films 215,127 may provide displacement constraints or force, such as large residual thin film stresses, to curve the flexible structure 213 in the desired deformation. A non-planar device may include a combination of pre-compressed, pre-stretched, or compressive films formed in a designated pattern to provide stress distributions according the designated pattern to achieve desired deformation of the device.

According to one embodiment, desired deformation may include chip bending curvature. For example, if flexible chips are to be deformed into a non-planar spherical patch from a planar disk, the required reduction in the circumference of the outer circle of the flexible chips can be calculated. In one embodiment, estimation of the chip bending curvature caused by deposited thin films with residual film stresses (on a relatively thick substrate) may be based on "Stoney Equation" (or approximation equation) when the displacement from the substrate bending is much less than the wafer thickness (e.g. thickness of device layers 205). For larger stresses on thin chips, numerical methods may be used to calculate the chip bending curvature without over-estimating the displacement via the approximation equation, as the displacement can easily be larger than the substrate thickness due to two-dimensional constraints.

Figure 3A:
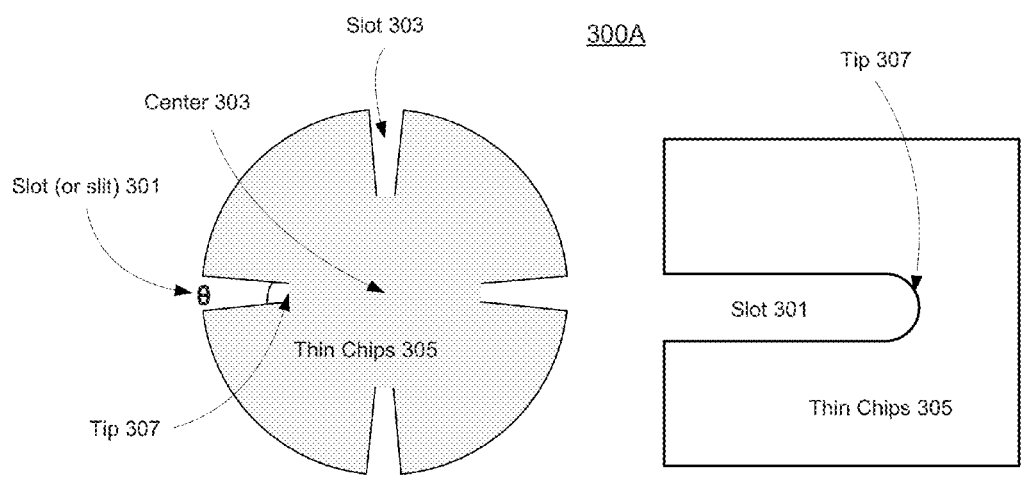
FIGS. 3A-3C are schematic diagrams illustrating exemplary non-planar chips based on slots according to embodiments described herein.
Figure 3B:
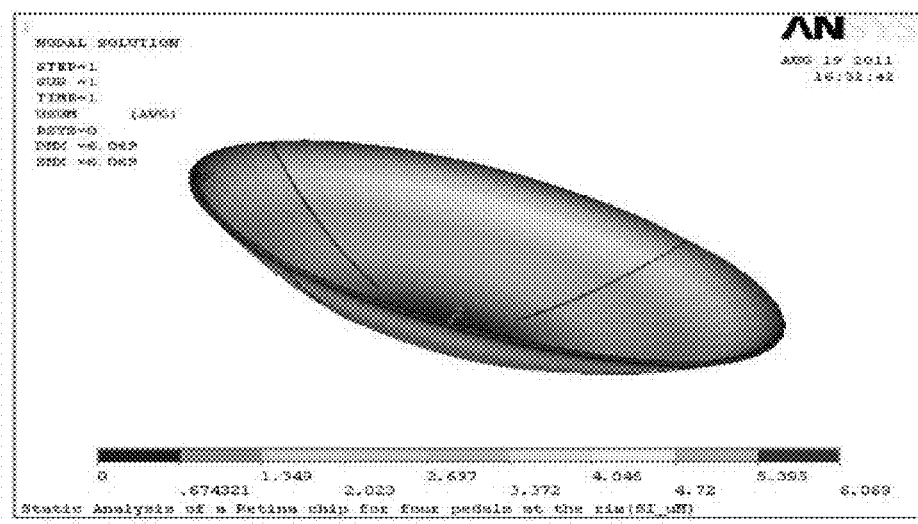
Figure 3C:
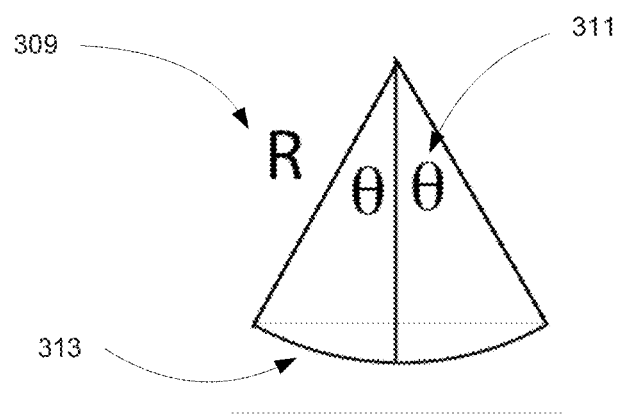

FIGS. 3A-3C are schematic diagrams illustrating exemplary non-planar chips based on slots according to embodiments described herein. For example, schematics 300A may include thin chips 305 of a thin die or wafer and exaggerated slot 301 with stress-relieve round corners at tip 307. When thin chips 305 is deformed, two sides of slot 301 may meet or close up. Thin chips 305 may be pre-stressed on a carrier substrate during fabrication process and become curved when released from the carrier substrate.

In one embodiment, thin chips 305 may comprise a circular chip with several radial slots (one or more) extending outward in the direction from the center of the circular chip (in a straight path or in a curved path, a spiral path, a zigzag path or other applicable paths) in fan/wedge shape with the surplus perimeters removed. The radial slots may extend from perimeter of thin chips 305 and stop at tips (e.g. fine tip about 1 μm in width) of the slots, such as tip 307 for slot 301, before (or at a distance from) reaching the center of thin chips 305. In one embodiment, tips of slots may be located within a thin chip to accommodate, for example, resolution limitation of micro fabrication process and/or increased stress intensity factors at the tip of the slot induced by chip deformation. Corners around tips of slots, such as around tip 307 of slot 301, may be rounded to reduce stress concentration associated with sharp corners and spread out stress over rounded slot corners when an associated chip is deformed or bended.

A slot may be formed by removing (or cutting, slitting), such as through deep reactive ion etching in the micro fabrication process, a portion of narrow channel area (e.g. a cutout, a longitudinal opening or narrow opening) of a chip, such as slot 301 of thin chips 305. The slot can reduce deformation stress, such as tangential in-plane stress, of the chip and increase allowable degrees of deformation of the chip. In one embodiment, the slot may break direct communication, within the chip, between circuit elements crossing the slots, thus jumpers (through the bonding pads to the constraining flex or another constraining chip, as will be described in the following), or longer power rails and data buses around the slots may be needed to distribute the power, ground & signal lines.

FIG. 3B shows a layered thin disk chip structure fabricated with slots and stressed films to bend or curve into a quasi-spherical patch and remain curved after release from a carrier wafer used during fabrication. Fixture structures may be bonded across the slots in the chip structure to prevent the curved chip from relaxing back to its original planar shape. The stress film may provide additional bending force to help constrain the chip to remain in a desired deformation. Although bending effect from stressed thin films on thin structures with one or more slots can greatly increase, large bending (e.g. 70-90 microns of edge displacement in the bending of a 30-micron thick retinal chip) may be associated with two dimensional constraints. Degrees of deformation may be measured, for example, in micros of edge displacement. As a result, relatively thicker films with large stresses (e.g. external bending) may be needed to achieve the desired large curvature.

FIG. 3C illustrates exemplary mechanisms to curve a planar chip. When a planar disk (e.g. including a planar chip) of diameter "d" is bent into a radius of curvature "R" 309, the angle 311 extended from the center of radius to the end points of a diameter line of the disk is 2θ, where $2R*\theta=d$. The original circumference of the disk is $S=\pi*d=2\pi R*\theta$; however, the deformed circumference 313 should be $S'=2\pi R*\sin(\theta)$ if the disk is deformed into a patch of a spherical shape. Since $\theta > \sin(\theta)$ when $\theta > 0$, the disk will experience in-plane tangential compressive stresses against the bending since there are excess of circumference $2\pi r*[-\sin(\theta)]$ at a radius r less or equal R. The slots remove such excess in an appropriate amount such that the two edges of the slot is brought together when the disk is deformed into a spherical shape. This principle of removing certain excess material from a planar chip into a curved non-planar shape may be applicable in some embodiments described herein.

Figure 4A:
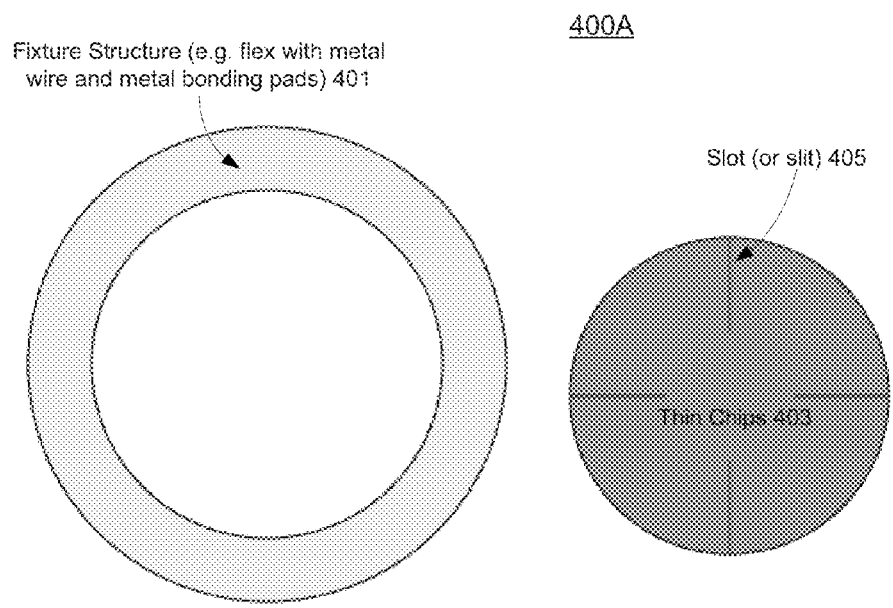
FIGS. 4A-4B are schematic diagrams illustrating exemplary embodiments of a thin chip assembled with a flex.
Figure 4B:
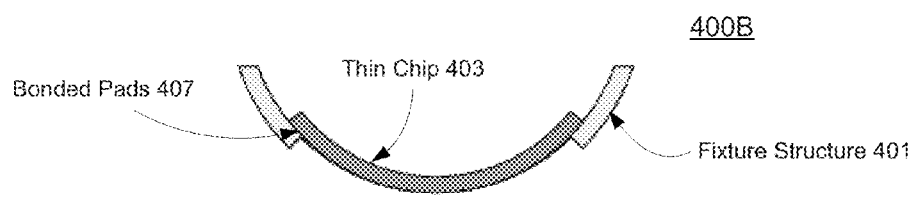

FIGS. 4A-4B are schematic diagrams illustrating exemplary embodiments of a thin chip assembled with a flex. Schematic 400A may include fixture structure 401 and thin chips 403. In one embodiment, fixture structure 401 may be a flex shaped in an annular ring (for example, formed from a flex "cable"). A flex may comprise a polymer (e.g. Polyamide) which can be transparent or translucent, deformable and/or moldable. In some embodiments, a flex may be shaped as a whole piece or in different applicable shapes according to desired deformation required. Thin chip 403 may be based on a thin wafer/die with slits for large deformation. In one embodiment, thin chips 403 may comprise flexible material with four slits (or slots), such as slot 405, to increase flexibility of the chip for large deformation. Fixture structure 401 may be bonded to flexible thin chip 403 to keep the chip in a bending state. The number and/or pattern of slots (e.g. 2, 12 or other applicable number of slots) formed on a thin chip may vary depending on desired deformation in the chip Turning now to FIG. 4B, assembly 400B may include curved thin chips 403 bonded with fixture structure 401 via, for example, bonded pads 407. Mechanical constraints from fixture structure 401 (or flex) may keep thin chips 403 to remain curved without relaxing back to its original flat state. Fixture structure 401 may include metal wires and metal bonding pads with appropriate thickness (for example, ~10 μm). Thin chips 403 may include matching (in relative location) bonding pads to be bonded with corresponding metal bonding pads of fixture structure 401. The metals may form thin-film bonding (for example, Au to Au) when under a pressure force in an elevated temperature (typically controlled within a range of 150 degree C. to 450 degree C.). The thin film bonding can also be used as electrical connections for data communication and power distribution.

FIGS. 5A-5F are block diagrams illustrating an exemplary sequence of assembly (or joining) process for a non-planar flexible device. For example, the non-planar flexible device may be fabricated or manufactured based on a curved thin wafer/die bonded with the flexible device via matching pads. At sequence 500A of FIG. 5A, in one embodiment, holder 501 may comprise a clear holder with recessed shapes, such as recess 503, to accommodate a flex or fixture structure. Recess 503 may accommodate flex material (e.g. polymer) which can be molded or shaped.

Figure 5A:
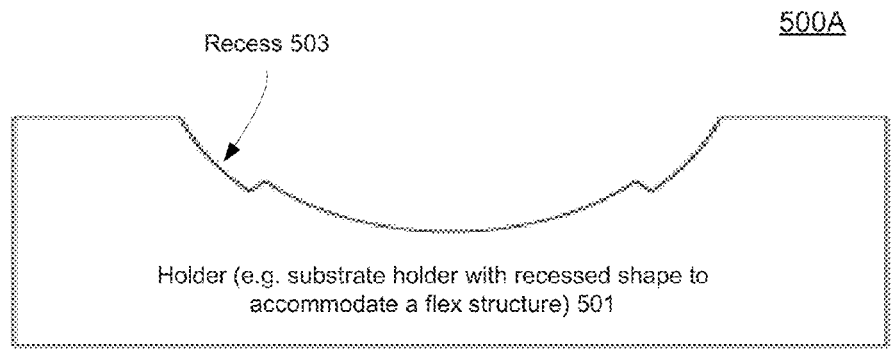
Figure 5B:
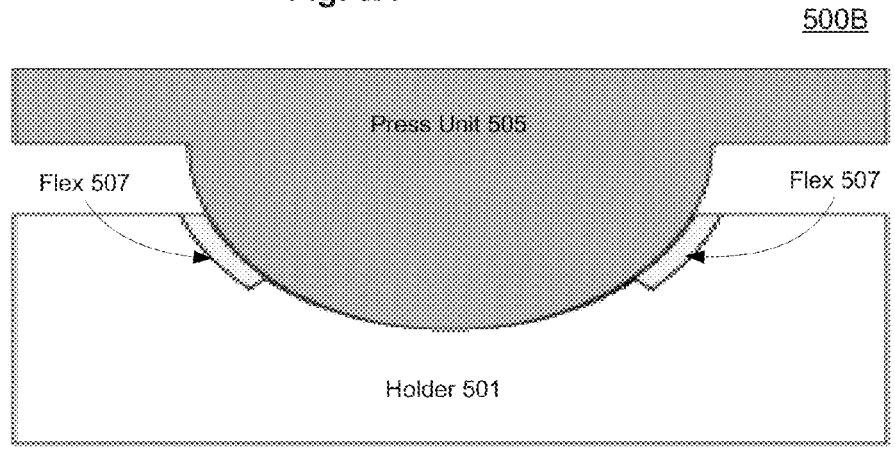
Figure 5C:
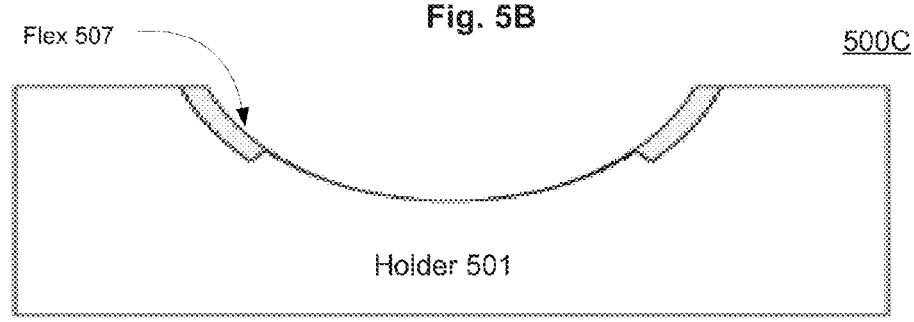

At sequence 500B of FIG. 5B, flex 507 may be tooled in recess 503. In one embodiment, press unit 505 and holder unit 501 may be brought together with pressure/heat applied to form flex 507 into a curved shape. Press unit 505 and holder unit 501 may be shaped with matching surfaces having a common or compatible radius of curvature. Flex 507 may be sandwiched between a press unit 505 (e.g. top unit) with spherical surface and holder unit 501 (e.g. bottom unit) with matching spherical recess. In one embodiment, flex 507 may comprise a polymer based ring held by vacuum (with vacuum holes on the surface of corresponding area, and vacuum channels inside holder 501) or by electrostatic force (e.g. using an electrostatic chuck). At sequence 500C of FIG. 5C, press unit 505 may be moved to separate from the holder unit 501 and leave flex 507 to remain deformed (or molded) in place (e.g. in recess 503). In some embodiments, thin chips bonded with a flex may be deformed based on mutual constraints between the flex and the thin chips without a need to mold the flex.

Turning now to FIG. 5D, at sequence 500D, press unit 505 and holder unit 501 may be brought together for bonding between thin chips (or wafer) 509 and flex 507 after press unit 517 and holder unit 501 are aligned. For example, thin chips 509 may be bonded or jointed with flex 507 at specific areas, such as bonding areas 511. Thin chip 509 may include metal based pads. Correspondingly, flex 507 may include matching pads. In one embodiment, press unit 505 may be aligned (e.g. via three dimensional rotational movements) with holder unit 501 to allow pads of thin chips 509 in contact with corresponding matching pads of flex 507. At least one of press unit 505 and holder unit 501 may be clear to allow the alignment. Press unit 505 of FIG. 5B and press unit 517 may be part of a plurality of press units with surfaces curved in different curvatures in one common assembly apparatus for non-planar devices.

In one embodiment, heat and pressure may be applied for bonding between thin chips 509 and flex 507, for example, to solder metal pads and corresponding matching pads together. Thin chips may be held on press unit (e.g. top press) 505, for example, via vacuum or electrostatics forces. Press 517 may be pressed against holder unit 501 after alignment of pads of thin chips 509 and matching pads of flex 507.

In some embodiments, flex 507 may be made through a clear bottom holder such as holder 501. Multiple layers of chips may be bonded via pressure and heat applied between a press unit and holder unit 501. Holder unit 501 may be associated with different shapes or styles of recesses to deform a flex or flexible chips, such as flex 507, depending on different chip designs. When the bonding is completed, at sequence 500E of FIG. 5E, press unit 505 may move away from holder unit 501 to release thin chip 509 bonded with flex 507 in a non-planar shape. Bonding pads may harden when cool down from bonding pressure/heat to cause separate chips/wafers to stick together (or bonded) in a curved or non-planar shape. In one embodiment, thin chips 509 bonded with flex 507 may be passivated (or coated) with barrier layers and/or polymer layers (e.g. to protect against corrosion) subsequent to sequence 5E. Air gaps between flex 507 (e.g. a separate chip mutually constrained to remain curved) and thin chips 509 may be backfilled with thermal conducting dielectric material for increase heat dissipation capability.

FIG. 5F shows an exaggerated view of a bonding pad between thin chips 509 and flex 507. For example, pad 513 of thin chips 509 may be bonded (or soldered) with matching pads 515 of flex 507. Pads 513 and matching pads 515 may comprise the same or different conducting material (e.g. gold). Bonding contact of a non-planar device, such as pads 513 bonded with matching pads 515, may be covered or coated (e.g. vapor coating or vacuum coating) with thin layer of hard passivation made of silicon nitride, diamond carbon or other applicable material to provide insulation and prevent exposing the bonding contact of the device. In one embodiment, bonding contacts may provide mechanical joining constraints and/or optional electrical connections between different portions of curved chips.

Figure 6A:
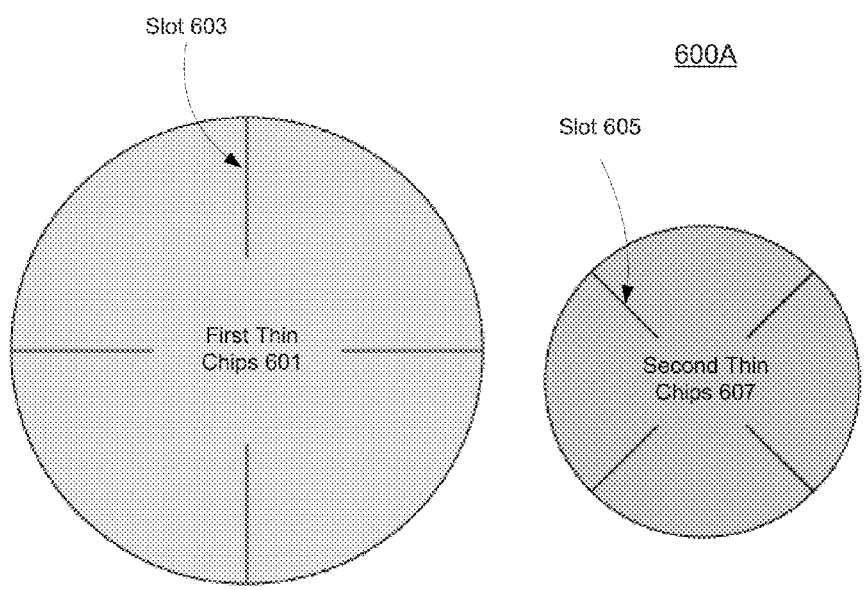
FIGS. 6A-6B are schematic diagrams illustrating exemplary embodiments of mutually constrained non-planar chips.
Figure 6B:
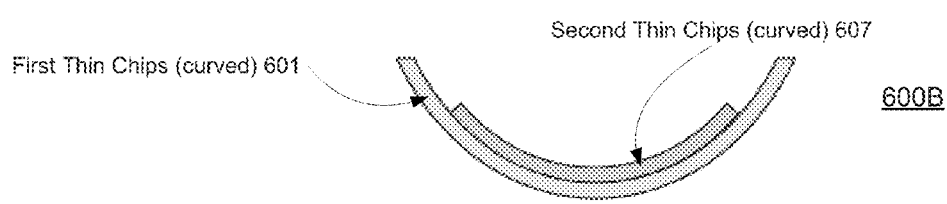

FIGS. 6A-6B are schematic diagrams illustrating exemplary embodiments of mutually constrained non-planar chips. For example, schematic 600A of FIG. 6A may illustrate two thin wafers/dies with off-set slits and matching bonding pads for mutual constraints for an assembly of curved chips. In one embodiment, first thin chips 601 and second thin chips 607 may each include four radial slots with matching metal bonding pads. Thin chips may be assembled with slots aligned with an angle. For example, slot 605 may cross slot 603 with a, for example, 45 degree angle in the assembled curved thin chips.

Turning now to FIG. 6B, assembly 600B may include first thin chips 601 and second thin chips 607 curved via mutual constraints. Assembled curved thin chips, such as first thin chip 601 and second thin chip 607, may not relax back to original flat or planar states because of mutual constraints applied to each other at bonding locations (e.g. bonding pad areas). In one embodiment, bonding pads may be paired across each slot of a thin chip to stick together portions of the chip across the slot.

Figure 7A:
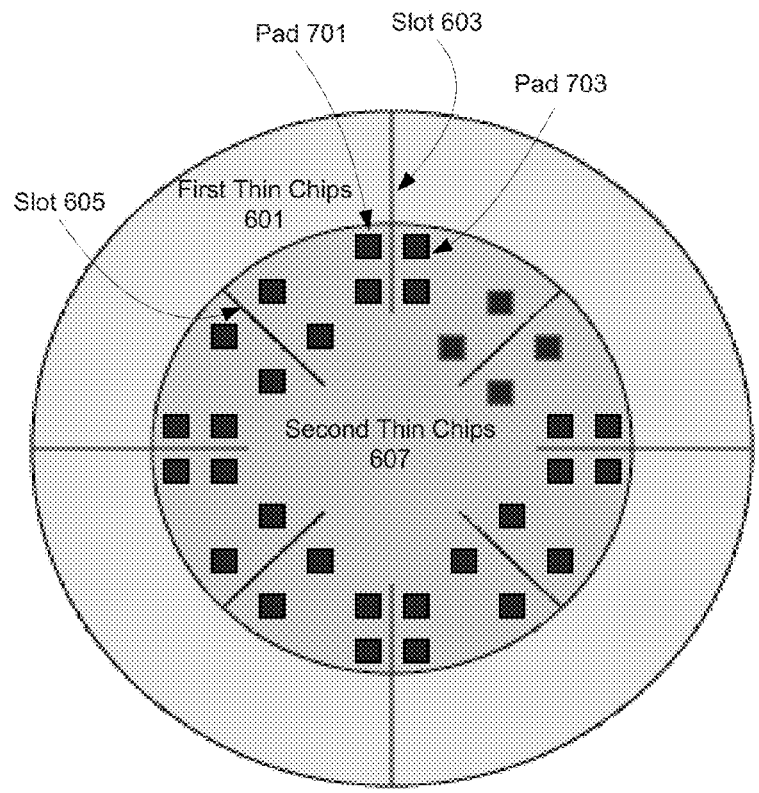
FIGS. 7A-7B are schematic diagrams illustrating exemplary top view and cross sectional view of an assembly with bonding pads.
Figure 7B:
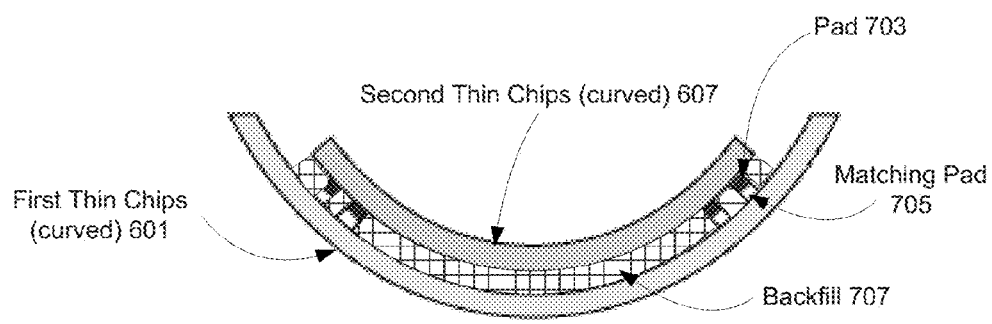

FIGS. 7A-7B are schematic diagrams illustrating exemplary top view and cross sectional view of an assembly with bonding pads. For example, FIG. 7A illustrates a top view of a non-planar 3D packaging of a stack of two thin chips, such as second thin chips 607 over first thin chips 601, curved into quasi-spherical shape. Neighboring slots between the stacked chips may be aligned with an angle (e.g. 45 degrees), such as slot 605 of second thin chips 607 and slot 603 of first thin chips 601. The bonding pads may be positioned on both sides of slots, such as pads 701 and pads 703 across slot 603.

FIG. 7B illustrates a cross sectional view (e.g. not to scale with exaggeration) of the thin film bonding with bond pads regions. For example, second thin chips 607 and first thin chips 601 may remain curved via bonding of pads, such as bonding between pad 703 and matching pad 705. Alternatively or optionally, thin chips may be bonded via glue to remain in a non-planar shape.

In one embodiment, a backfill layer, such as backfill 707, between adjacent chips of a non-planar assembly stacking multiple chips may facilitate heat dissipation between the chips. A backfill layer may comprise thermal conductive dielectric material to control the temperature rise of the assembled structure (or non-planar chips) in operation. For example, heat generated from high speed processing circuitry embedded inside a non-planar assembly may be allowed to pass through both bonding pads and backfill layers to help cool down the non-planar assembly. In one embodiment, a backfill layer may reduce or eliminate thermal insulation of air gaps in a non-planner assembly. Alternatively, the non-planar assembly may be immersed in a liquid, such as silicon oil, to fill up air gaps to provide cooling effects.

The stack is not limited to two layers, or limited to round shapes. Multiple chips non-planar 3D stack with staggered slots can be formed. Power, signals and data can jump between layers to cross the slots to distribute electrical power and signals between stacked pieces and adjacent pieces. Since the active devices will be under bending stresses, the stress-induced effects such as the increase of trans-conductance for tensile stresses in both longitudinal and transverse directions on N-type MOS transistors, and either increase or decrease in the case of P-type transistors may be taken into account and pre-compensated in the system design.

Figure 8A:
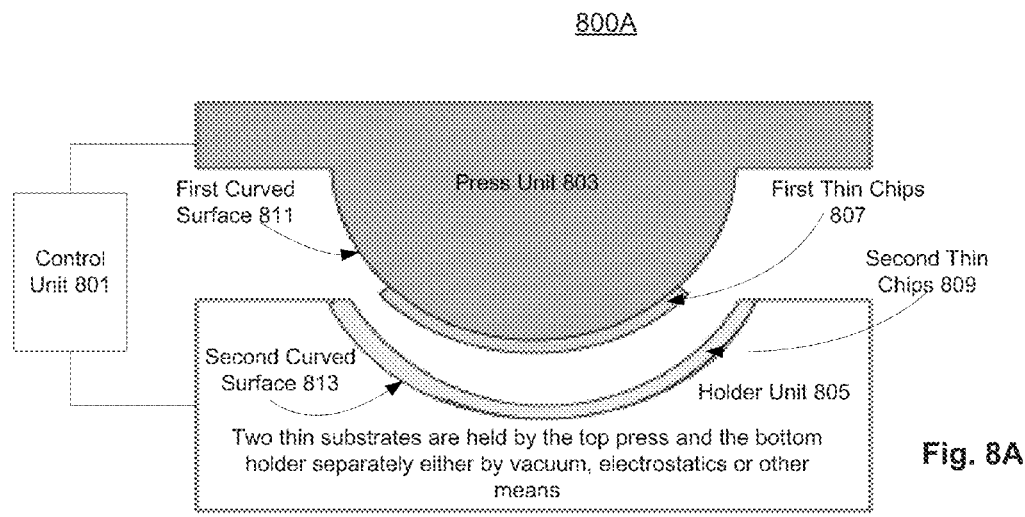
FIGS. 8A-8C are block diagrams illustrating an exemplary sequence to assemble curved stack of thin dies/wafers in one embodiment described herein.
Figure 8B:
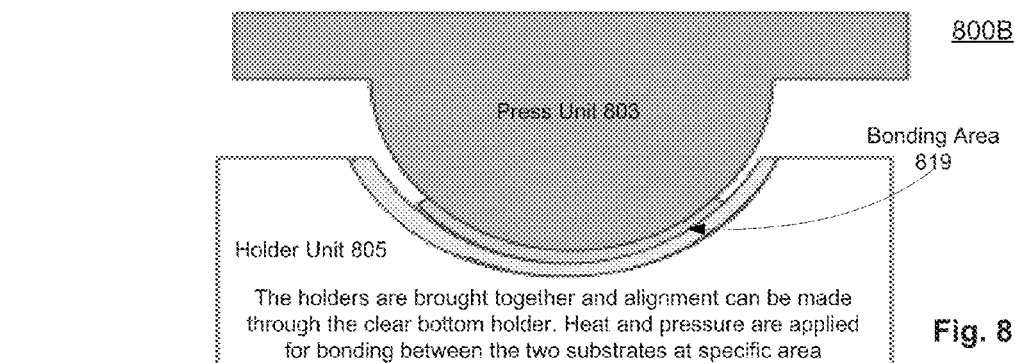
Figure 8C:
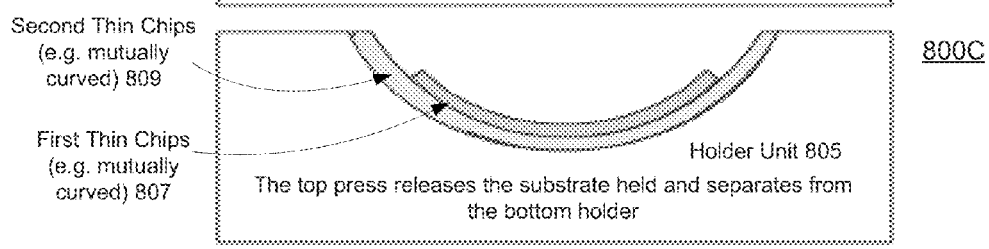

FIGS. 8A-8C are block diagrams illustrating an exemplary sequence to assemble curved stack of thin dies/wafers or substrates in one embodiment described herein. For example, at sequence 800A of FIG. 8A, two thin chips, first thin chips 807 and second thin chips 809, may be held in an assembly apparatus. In one embodiment, the assembly apparatus may include press unit 803 (e.g. upper unit), holder unit 805 (e.g. lower unit) and a control unit 801. Press unit 803 and/or holder unit 805 may move in a three dimensional manner including translational and/or rotational movements, for example, controlled by control unit 801.

In one embodiment, first thin chip 807 and second thin chip 809 may be separately held by press unit 803 and holder unit 805 either by vacuum, electrostatics or other means. For example, press unit 803 or holder unit 805 may comprise vacuum chucks with rings of small holes or openings of vacuum channels to provide suction forces to hold thin chips. Press unit 803 and holder unit 805 may be associated with matching surfaces to deform the thin chips held. In one embodiment, first thin chips 807, when held by press unit 803, may be deformed over first curved surface 811 of press unit 803. Second thin chips 809, when held by holder unit 805, may be deformed over second curved surface 813 of holder unit 805. First thin chips 807 and/or second thin chips 809 may include slots to increase flexibility of the chips to deform (or curve, bend). First curved surface 811 and second curved surface 813 may be of a common curvature to match each other.

At sequence 800B of FIG. 8B, holders may be brought together after alignment. For example, holder unit 805 may be clear or transparent to allow alignment with press unit 803 via first chin chips 807 and second thin chips 809. In one embodiment, alignment between holders may be based on matching corresponding bonding pads between first thin chips 807 and second thin chips 809 (e.g. based on masks).

Press unit 803 may rotate in three rotational dimensions for aligning chips held. In one embodiment, press unit 803 may be constrained to move in one translational dimension, for example, towards or away from holder unit 805, to allow surfaces of holders, e.g. first curved surface 811 and second curved surface 813, to match each other. In some embodiments, surfaces of the holders may match with a common center of curvature (or ball center).

As press unit 803 and holder unit 805 are brought together, heat and pressure may be applied for bonding between first thin chips 807 and second thin chips 809 at specific area of thin metal film bonding region, such as bonding area 819. Thin metal film bonding region may include pads aligned with matching pads between the thin chips. In one embodiment, pads may melt together using controlled ranges of elevated temperatures. For example, heat of about 100-180 degrees C. (Celsius) may be used for tin/lead based pads. Alternatively, heat of about 350-450 degrees C. may be needed for pads made of gold alloy.

At sequence 800C of FIG. 8C, press unit 803 may release first chips 807 held and separate itself from holder unit 805. A non-planar assembly including first chips 807 bonded with second chips 809 may remain curved via mutual constraints provided from established bonding between the chips.

In the foregoing specification, the invention has been described with reference to specific exemplary embodiments thereof. It will be evident that various modifications may be made thereto without departing from the broader scope of the invention as set forth in the following claims. The invention is not limited to the particular forms, drawings, scales, and detailed information disclosed. The specification and drawings are, accordingly, to be regarded in an illustrative sense rather than a restrictive sense.

What is claimed is:

1. An implant apparatus comprising:
   a plurality of photo sensors to receive light;
   a plurality of micro electrodes to stimulate neuron cells for enabling perception of a vision of the light captured by the photo sensors;
   a plurality of guard rings, each micro electrode surrounded by one of the guard rings to provide local return paths to confine electric flows from the electrode to targeted neuron cells, wherein the guard ring serves as a local return electrode corresponding to the micro electrode to prevent the electric flows from being toward undesired target directions; and
   circuitry coupled to the photo sensors and the micro electrodes, the circuitry to drive the micro electrodes for the stimulation of the neuron cells, wherein the apparatus is implemented in an integrated semiconductor device with a bendable flexibility to conform to a shape of a human eyeball and allow the micro electrodes in close proximity to the neuron cells for the stimulation.

2. The apparatus of claim 1, wherein each micro electrode is sized to target a small number of separate neuron cells.

3. The apparatus of claim 1, wherein the micro electrodes are distributed in a quasi-spherical geometry based on the shape of a human eyeball.

4. The apparatus of claim 1, wherein the semiconductor device includes an array of pixel units, and wherein each pixel unit includes one of the micro electrodes, one of the guard rings surrounding the one electrode, one of the photo sensors, and corresponding circuitry.

5. The apparatus of claim 4, wherein the array of pixel units comprises a microelectrode array having a density higher than 250 microelectrodes per square millimeter.

6. The apparatus of claim 4, wherein the device comprises layered structures including a semiconductor layer and metal interconnect layers, wherein the semiconductor layer includes the photo sensors and transistors for the circuitry, the micro electrodes coupled with the circuitry via the metal interconnect layers.

7. The apparatus of claim 6, wherein the semiconductor device has a front side and a back side opposite to the front side, wherein the semiconductor layer is positioned in the layered structure close to the front side of the semiconductor device and wherein the substrate layer is positioned in the layered structure close to a back side of the semiconductor device.

8. The apparatus of claim 7, wherein the semiconductor device allows the light to reach photo sensors in the semiconductor layer from the front side.

9. The apparatus of claim 7, wherein the micro electrodes are in contact with the neuron cells from the front side of the semiconductor device.

10. The apparatus of claim 7, wherein the micro electrodes are in contact with the neuron cells from the back side of the semiconductor device, wherein the layered structures include through-silicon vias to join the metal interconnect layer and the micro electrodes.

11. The apparatus of claim 1, wherein the photo sensors and the micro electrodes are arranged to face opposite sides of the semiconductor device and wherein the semiconductor is configured to allow the light to reach the photo sensors from one of the sides with the micro electrodes.

12. The apparatus of claim 11, wherein the substrate is thinned to allow the photo sensors to absorb the light through the substrate.

13. The apparatus of claim 12, wherein the substrate has a thickness of about less than 20 microns.

14. The apparatus of claim 1, wherein thickness of the semiconductor device is sized to allow the photo sensors to capture the light from either sides of the semiconductor device.

15. The apparatus of claim 1, wherein the stimulation is based on the electric flows from the electrodes to the neuron cells, and wherein the local return paths are provided based on low impedance current path selection.

16. The apparatus of claim 1, wherein the apparatus is suitable of being implanted within living tissues, and wherein the semiconductor device is sealed within biocompatible layers to provide bi-directional protection between the living tissues and the layered structures.

17. The apparatus of claim 16, wherein at least one of the micro electrodes include protruding tips over the biocompatible layer to increase proximity between the at least one electrodes and targeted neuron cells.

18. The apparatus of claim 17, wherein the protruding tips are arranged in one or more protruding layers of different heights above a surface of the semiconductor device to allow micro electrodes of different layers to access different layers of the neuron cells.

19. The apparatus of claim 4, wherein the circuitry includes a plurality of processing circuitry, each pixel unit including one of the plurality of processing circuitry, wherein the pixel units are arranged as a network with interconnects to allow processing circuitry of each pixel unit to derive a stimulus from the light received via the pixel unit and at least one other pixel unit of the network via the interconnects.

20. The apparatus of claim 19, wherein the pixel unit is associated with at least one neighboring pixel units according to the array and wherein the at least one other pixel units include the neighboring pixel units of the pixel unit.

21. An apparatus implementable to tissues including neuron cells, comprising:
 a plurality pixel units arranged in a two dimensional array to enable perception of
  a vision of light incoming to the pixel units, each pixel unit comprising a photo sensor to receive the light,
  a micro electrode to deliver a stimulus to targeted ones of the neuron cells for the perception,
  a guard ring surrounding the micro electrode to confine electric flows of the stimulus from the electrode to the targeted neuron cells, wherein the guard ring serves as a local return electrode corresponding to the micro electrode to prevent the electric flows from being toward undesired target directions, and
  circuitry to derive the stimulus from the light and drive the electrode, wherein the two dimensional array is arranged within a semiconductor device having a front surface and a back surface opposite to the front surface; and
 biocompatible layers wrapping the device to bi-directionally protect the device and the tissues, the biocompatible layers having openings to allow electrodes of the pixel units to stimulate the neuron cells,
 wherein the device comprises flexible material to allow the device to be bendable in a two dimension manner to conform to a shape of a human eyeball and
 wherein the flexible material is translucent to enable the device to receive the light from either the front surface or the back surface of the device.

22. The apparatus of claim 21, further comprising:
 a plurality perforation holes through the device to allow fluidic flow between the front surface and the back surface passing the perforation holes.

23. An integrated semiconductor device for retina prosthesis, the device comprising:
 an array of pixel units to enable perception of a vision of light, each pixel unit comprising
  a sensor to sense the light,
  an electrode to deliver a stimulus to targeted ones of neuron cells for the perception,
  a guard ring surrounding the electrode to provide local return paths to confine electric flows from the electrode to the targeted neuron cells, wherein the guard ring serves as a local return electrode corresponding to the micro electrode to prevent the electric flows from being toward undesired target directions, and
  circuitry to derive the stimulus from the light to drive the electrode,
 wherein the array of pixel units are arranged with a density of higher than 250 electrodes per square millimeter in the device, and
 wherein the device is bendable to allow the array of pixel units to conform to a radius of curvature of at least 12.5 millimeter according to a shape of a human eyeball.

* * * * *